United States Patent [19]

Adams et al.

[11] Patent Number: 5,464,431
[45] Date of Patent: Nov. 7, 1995

[54] ATRIAL FIBRILLATION DETECTOR

[75] Inventors: John M. Adams, Issaquah; Clifton A. Alferness, Redmond, both of Wash.

[73] Assignee: InControl, Inc., Redmond, Wash.

[21] Appl. No.: 410,829

[22] Filed: Mar. 27, 1995

Related U.S. Application Data

[60] Division of Ser. No. 306,665, Sep. 15, 1994, which is a continuation-in-part of Ser. No. 96,029, Jul. 22, 1993, abandoned, which is a continuation of Ser. No. 684,130, Apr. 12, 1991, Pat. No. 5,282,837.

[51] Int. Cl.$^6$ .................................................. A61N 1/39
[52] U.S. Cl. .................... 607/4; 607/16; 607/5; 128/702; 128/705
[58] Field of Search .................. 607/16, 18–26, 607/5, 4; 128/702, 705

[56] References Cited

U.S. PATENT DOCUMENTS 3,952,750  4/1976  Mirowski et al. .................. 128/419
4,202,340  5/1980  Langer et al. .................. 607/5
4,860,751  8/1989  Callaghan .................. 607/19

OTHER PUBLICATIONS

*Advances in Third Generation ICD Therapy*, Hook et al., CARDIO, Nov., 1991, pp. 66–72.

*Primary Examiner*—William E. Kamm
*Assistant Examiner*—Kennedy J. Schaetzle
*Attorney, Agent, or Firm*—Richard O. Gray, Jr.

[57] ABSTRACT

An atrial defibrillator implantable beneath the skin of a patient includes an intervention sequencer for performing an intervention sequence. The intervention sequencer includes an atrial fibrillation detector for determining if atrial fibrillation is present in a patient's heart and a cardiovertor for applying cardioverting electrical energy to the atria of the patient's heart if the atrial fibrillation detector determines that atrial fibrillation is present. A sequence initiating stage includes a receiver for receiving a sequence command generated from external to the patient. The sequence initiating stage causes the intervention sequencer to perform the intervention sequence upon receipt of a sequence command.

1 Claim, 8 Drawing Sheets

ATRIAL FIBRILLATION DETECTOR

RELATED APPLICATIONS

This application is a divisional of pending U.S. application Ser. No. 08/306,665, filed Sep. 15, 1994, entitled ATRIAL DEFIBRILLATOR HAVING PATIENT ACTIVATED MODALITY, which, in turn, is a continuation-in-part of application Ser. No. 08/096,029, filed Jul. 22, 1993, entitled METHOD FOR CARDIOVERTING THE ATRIA OF THE HEART, now abandoned, which, in turn, is a continuation application of Ser. No. 07/684,130, filed Apr. 12, 1991, entitled ATRIAL DEFIBRILLATOR AND METHOD, now U.S. Pat. No. 5,282,837.

BACKGROUND OF THE INVENTION

The present invention generally relates to an implantable atrial defibrillator for applying cardioverting electrical energy to the atria of a patient's heart in need of cardioversion. The present invention is more particularly directed to such a defibrillator which is programmable into a fully automatic mode, a patient activated mode, or a combined automatic and patient activated mode. The atrial defibrillator includes an intervention sequencer which is utilized in all of the selectable modes. The intervention sequencer includes an atrial fibrillation detector for determining if the atria are in need of cardioversion and a cardiovertor for applying cardioverting electrical energy to the atria of the heart.

Atrial fibrillation is probably the most common cardiac arrhythmia. Although it is not usually a life threatening arrhythmia, it is associated with strokes thought to be caused by blood clots forming in areas of stagnant blood flow as a result of prolonged atrial fibrillation. In addition, patients afflicted with atrial fibrillation generally experience palpitations of the heart and may even experience dizziness.

Atrial fibrillation occurs suddenly and many times can only be corrected by a discharge of electrical energy to the heart through the skin of the patient by way of an external defibrillator of the type well known in the art. This treatment is commonly referred to as synchronized cardioversion and, as its name implies, involves applying electrical defibrillating energy to the heart in synchronism with a detected ventricular electrical activation (R wave) of the heart. The treatment is very painful and, unfortunately, most often only results in temporary relief for patients, lasting but a few weeks.

Drugs are available for reducing the incidence of atrial fibrillation. However, these drugs have many side effects and many patients are resistant to them which greatly reduces their therapeutic effect.

Implantable atrial defibrillators have been proposed to provide patients suffering from occurrences of atrial fibrillation with relief. Unfortunately, to the detriment of such patients, none of these atrial defibrillators have become a commercial reality.

Two such proposed defibrillators, although represented as being implantable, were not fully automatic, requiring human interaction for cardioverting or defibrillating the heart. Both of these proposed defibrillators required the patient to recognize the symptoms of atrial fibrillation with one defibrillator requiring a visit to a physician to activate the defibrillator and the other defibrillator requiring the patient to activate the defibrillator with an external magnet. Neither defibrillator included an atrial fibrillation detector or detected atrial activity of the heart. As a result, these manually operated defibrillators provided no atrial fibrillation detection support for the patient.

An improved implantable atrial defibrillator which is automatic in operation is fully described in U.S. Pat. No. 5,282,837. The atrial defibrillator disclosed in this patent is truly automatic by including an atrial fibrillation detector which, responsive to sensed atrial activity, determines when the atria of the heart are in need of cardioversion. When the atrial fibrillation detector determines that the atria are in fibrillation and thus in need of cardioversion, the atrial fibrillation detector causes a cardiovertor stage to deliver defibrillating or cardioverting electrical energy to the atria in timed relation to a detected ventricular electrical activation (R wave) of the heart. As a result, the atria are automatically and safely cardioverted.

Because atrial fibrillation, unlike ventricular fibrillation, is generally not immediately life threatening, a fully automatic atrial defibrillation modality may not be necessary for a great number of patients, and especially for those patients who are highly symptomatic. Further, some patients may wish to control when cardioverting therapy is to be delivered. However, even though some patients may be able to accurately diagnose when their heart is experiencing an episode of atrial fibrillation, it would still be desirable to provide a manual or patient activated modality which includes automatic atrial fibrillation detection to confirm the patient's own diagnosis. Hence, if the patient has a perceived atrial fibrillation episode and activates the defibrillator, it would be beneficial to the patient that the defibrillator, prior to cardioversion, confirm, through an atrial fibrillation detector, that atrial fibrillation is actually present. In this way, the patient will not be subjected to unnecessary cardioversion attempts which otherwise may cause discomfort to the patient and early depletion of the defibrillator power source.

Still other patients may benefit from a combined patient activated and fully automatic modality. For example, patients which are symptomatic some of the time would fall into this category. Such combined modalities must be coordinated and provide atrial fibrillation detection and confirmation to assure that unnecessary cardioversion attempts are not delivered. The present invention provides an atrial defibrillator which satisfies all of these requirements.

SUMMARY OF THE INVENTION

The present invention therefore provides an atrial defibrillator implantable beneath the skin of a patient which includes intervention sequence means for performing an intervention sequence, the intervention sequence means including an atrial fibrillation detector for determining if atrial fibrillation is present in a patient's heart and cardioverting means for applying cardioverting electrical energy to the atria of the patient's heart. The atrial defibrillator further includes sequence initiating means including receiving means for receiving a sequence command generated form external to the patient for causing the intervention sequence means to perform the intervention sequence.

The present invention further provides an atrial defibrillator implantable beneath the skin of a patient, including intervention sequence means for performing an intervention sequence. The intervention sequence means includes an atrial fibrillation detector for first determining if atrial fibrillation is present in a patient's heart and cardioverting means for next applying cardioverting electrical energy to the atria of the patient's heart if the atrial fibrillation detector determines that atrial fibrillation is present. The atrial defibrillator further includes sequence initiating means including receiving means for receiving a sequence command generated form external to the patient for causing the intervention sequence means to perform the intervention sequence.

The atrial defibrillator may further include programming means responsive to mode commands generated from external to the patient. In accordance with one aspect of the present invention, the programming means is responsive to a patient activated mode command for causing the sequence initiating means to activate the intervention sequence means only in response to the sequence command generated from external to the patient and an automatic mode command for causing the Sequence initiating means to activate the intervention sequence means at predetermined times. In accordance with a further aspect of the present invention, the programming means is responsive to a patient activated mode command for causing the sequence initiating means to activate the intervention sequence means only in response to the sequence command generated from external to the patient and responsive to a combined automatic and patient activated mode command for causing the sequence initiating means to activate the intervention sequence means both in response to the sequence command generated from external to the patient and at predetermined times.

The present invention further provides an apparatus for administering electrotherapy to a patient's heart to restore a normal heart rhythm. The apparatus includes an unsophisticated primary detector means for detecting, with a first degree of precision, possible abnormalities in a patient's heart rhythm, and a sophisticated secondary detector means for analyzing the heart rhythm and more precisely identifying abnormalities therein, the secondary detector means being generally inactive in regard to detecting and analyzing abnormalities in the heart rhythm in the absence of a detection of a possible abnormality by the primary detector means. The apparatus further includes means responsive to the detection of a possible abnormality in the heart rhythm by the primary detector means for activating the secondary detector means, the secondary detector means being constructed and arranged to analyze the patient's heart rhythm with a second degree of precision significantly higher than the first degree of precision exercised by the primary detector means in order to confirm the rhythm abnormality, and means responsive to confirmation of the rhythm abnormality by the secondary detector means for delivering appropriate electrocardiac therapy to the heart.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawing, in the several figures of which like reference numerals identify identical elements, and wherein:

DETAILED DESCRIPTION OF THE PREFERRED EMBODIMENT

Figure 1:
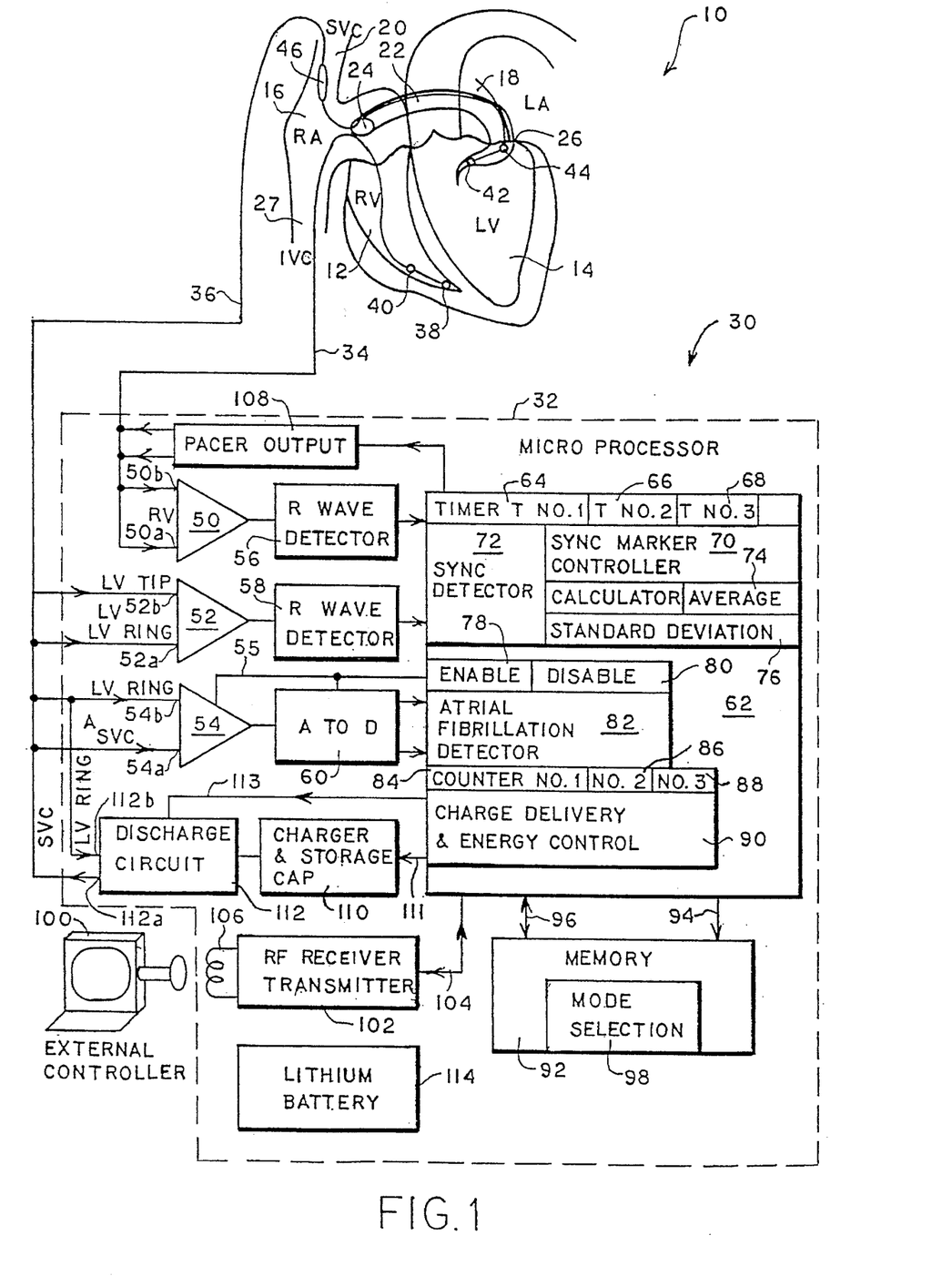
FIG. 1 is a schematic block diagram of a fully implantable atrial defibrillator embodying the present invention for applying defibrillating electrical energy to the atria of a human heart and which is shown in association with a human heart in need of atrial fibrillation monitoring and potential cardioversion of the atria.

Referring now to FIG. 1, it illustrates a fully implantable atrial defibrillator 30 embodying the present invention shown in association with a schematically illustrated human heart 10 in need of atrial fibrillation monitoring and potential cardioversion of the atria. The portions of the heart 10 illustrated in FIG. 1 are the right ventricle 12, the left ventricle 14, the right atrium 16, the left atrium 18, the superior vena cava 20, the coronary sinus 22, the coronary sinus ostium or opening 24, the left ventricular free wall 26 and the inferior vena cava 27. In addition, as used herein, the terms "electrical activations" or "ventricular activations" denote R waves of the heart cardiac cycle which induce depolarizations of the ventricles.

The atrial defibrillator 30 generally includes an enclosure 32 for hermetically sealing the internal circuit elements of the atrial defibrillator to be described hereinafter, an endocardial first lead 34, and an intravascular second lead 36. The enclosure 32 and first and second leads 34 and 36 are arranged to be implanted beneath the skin of a patient so as to render the atrial defibrillator 30 fully implantable.

The endocardial first lead 34 preferably comprises a endocardial bi-polar lead having electrodes 38 and 40 arranged for establishing electrical contact with the right ventricle 12 of the heart 10. The electrodes 38 and 40 permit bi-polar sensing of electrical activations in the right ventricle. As illustrated, the lead 34 is fed through the inferior vena cava 27, into the right atrium 16, and then into the right ventricle 12, as illustrated. As will be appreciated by those skilled in the art, a second path for lead 34 could alternatively be through the superior vena cava 20, into the right atrium 16, and then into the right ventricle 12.

The second lead 36 generally includes a first or tip electrode 42, a second or ring electrode 44, and a third electrode 46. As illustrated, the second lead 36 is flexible and arranged to be passed down the superior vena cava 20, into the right atrium 16, into the coronary sinus ostium 24, and advanced into the coronary sinus 22 of the heart near the left side thereof so that the first or tip electrode 42 is within the coronary sinus adjacent the left ventricle 14. The electrodes 42, 44, and 46 are spaced apart such that when the first electrode 42 is within the coronary sinus 22 adjacent the left ventricle 14, the second electrode 44 is beneath the left atrium 18 near the left ventricle 14, and the third electrode 46 is in a region adjacent to the right atrium coronary sinus ostium 24 within either the right atrium 16 or the superior vena cava 20. The first electrode 42 and the second electrode 44 enable bi-polar sensing of electrical activations of the left ventricle 14. The second electrode 44 together with the third electrode 46 provide bi-polar sensing of heart activity in the atria 16 and 18. The second electrode 44 and the third electrode 46 further provide for the delivery of defibrillating electrical energy of the atria. Because the second electrode 44 is located beneath the left atrium 18 near the left ventricle 14, and the third electrode 46 is within either the right atrium 16 or the superior vena cava 20 and above the coronary sinus ostium 24, the electrical energy applied between these electrodes will be substantially confined to the atria 16 and 18 of the heart 10. As a result, the electrical energy applied to the right ventricle 12 and left ventricle 14 when the atria are cardioverted or defibrillated will be minimized. This greatly reduces the potential for ventricular fibrillation of the heart to be induced as a result of the application of defibrillating electrical energy of the atria of the heart.

Within the enclosure 32, the atrial defibrillator 30 includes a first sense amplifier 50, a second sense amplifier 52, and a third sense amplifier 54. The first sense amplifier 50 forms a first sensing means which, together with the first lead 34 to which it is coupled, senses electrical activations of the right ventricle 12. The second sense amplifier 52 forms a second sensing means which, together with the first electrode 42 and second electrode 44 of the second lead 36 to which it is coupled, senses electrical activations of the left ventricle 14. The third sense amplifier 54 forms atrial sense means which, together with the second electrode 44 and third electrode 46 of the second lead 36 to which it is coupled, senses atrial activity of the heart when enabled as will be described hereinafter.

The outputs of the first and second sense amplifiers 50 and 52 are coupled to first and second R wave detectors 56 and 58 respectively. Each of the R wave detectors 56 and 58 is of the type well known in the art which provides an output pulse upon the occurrence of an R wave being sensed during a cardiac cycle of the heart. The output of the third sense amplifier 54 is coupled to an analog-to-digital convertor 60 which converts the analog signal representative of the atrial activity of the heart being sensed to digital samples for processing when the analog-to-digital convertor 60 is enabled also in a manner to be described hereinafter.

The enclosure 32 of the atrial defibrillator 30 further includes a microprocessor 62. The microprocessor 62 is preferably implemented in a manner to be described hereinafter with respect to the flow diagrams of FIGS. 2 through 6. The implementation of the microprocessor 62 results in a plurality of functional stages. The stages include a first timer 64, a second timer 66, a third timer 68, a synchronization marker controller 70, and a synchronization detector 72. The functional stages of the microprocessor 62 further include a calculator stage including an average calculation stage 74, a standard deviation calculation stage 76, an enable stage 78, a disable stage 80, an atrial arrythmia detector in the form of an atrial fibrillation detector 82, a first counter 84, a second counter 86, a third counter 88, and a charge delivery and energy control stage 90.

The microprocessor 62 is arranged to operate in conjunction with a memory 92. The memory 92 is coupled to the microprocessor 62 by a multiple-bit address bus 94 and a bi-directional multiple-bit data bus 96. The address bus 94 permits the microprocessor 62 to address desired memory locations within the memory 92 for executing write or read operations. During a write operation, the microprocessor stores data, such as time intervals or operating parameters, in the memory 92 at the addresses defined by the multiple-bit addresses conveyed over bus 94, and coveys the data to the memory 92 over the multiple-bit bus 96. During a read operation, the microprocessor 62 obtains data from the memory 92 from the storage locations identified by the multiple-bit addresses provided over bus 94, and receives the data from the memory 92 over the bi-directional bus 96.

For entering operating parameters into the memory 92, the microprocessor 62 receives programmable operating parameters from an external controller 100 which is external to the skin of the patient. The external controller 100 is arranged to communicate with a receiver/transmitter 102 which is coupled to the microprocessor 62 over a bi-directional bus 104. The receiver/transmitter 102 may be of the type well known in the art for conveying various information which it obtains from the microprocessor 62 to the external controller 100, or for receiving programming parameters from the external controller 100 which the receiver/transmitter 102 then conveys to the microprocessor 62 for storage in the memory 92. To that end, the memory 92 includes a mode selection portion 98 for storing mode selection information, to be described hereinafter.

The receiver/transmitter 102 includes a transmitting coil 106 so that the receiver/transmitter 102 and coil 106 form a communication means. Such communication means are well known in the art and may be utilized as noted above for receiving commands from external to the implantable enclosures 32, and for transmitting data to the external controller 100 from the implanted enclosure 32. One such communication system is disclosed, for example, in U.S. Pat. No. 4,586,508.

To complete the identification of the various structural elements within the enclosure 32, the atrial defibrillator 30 further includes a pacer output stage 108. As will be seen hereinafter, the pacer output stage 108 applies stimulating pulses to the right ventricle 12 of the heart 10 when bradycardia pacing is required, or synchronization marker pulses to the right ventricle when the atrial defibrillator is in the marker pulse mode. The atrial defibrillator 30 further includes a charger and storage capacitor circuit 110 of the type well known in the art which charges a storage capacitor to a predetermined voltage level and a discharge circuit 112 for discharging the storage capacitor within circuit 110 by a predetermined amount to provide a controlled discharge output of electrical energy when required to the atria of the heart. To that end, the discharge circuit 112 is coupled to the second electrode 44 and the third electrode 46 of the second lead 36 for applying the cardioverting or defibrillating electrical energy to the atria. Lastly, the defibrillator 30 includes a depletable power source 114, such as a lithium battery, for providing power to the electrical components of the atrial defibrillator 30. As will be seen hereinafter, the atrial defibrillator 30 is arranged to minimize the power consumption of the battery 114 so as to extend the useful life of the atrial defibrillator 30.

Figure 2:
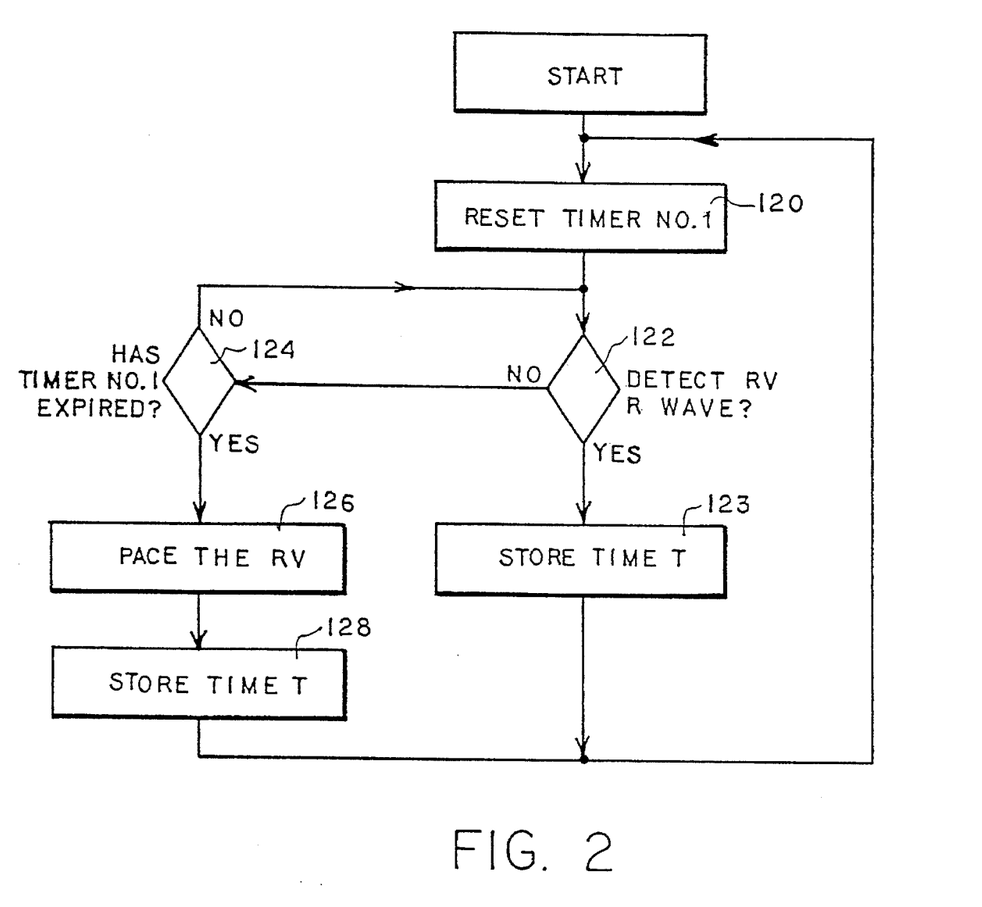
FIG. 2 is a flow diagram illustrating the manner in which the atrial defibrillator of FIG. 1 may be implemented for providing bradycardia pacing of the right ventricle of the heart and for determining and storing the time intervals between depolarizations of the right ventricle.

The operation of the atrial defibrillator 30, and more particularly the operation of the functional stages residing within the enclosure 32, will now be described with reference to the flow diagrams of FIGS. 2–6. Referring now to FIG. 2, it illustrates the manner in which the atrial defibrillator 30 may be implemented in accordance with the present invention for providing bradycardia pacing of the right ventricle 12 of the heart 10 and the determining of the time intervals between electrical activations of the right ventricle or bradycardia pacing pulses of the right ventricle. This process begins with the resetting of the first timer 64 in step 120. The microprocessor then, in step 122, determines whether an R wave has been detected at the right ventricle. If an R wave has not been detected at the right ventricle, the processor then determines in step 124 if the first timer 64 has expired. If the first timer 64 has not expired, the processor returns to step 122 to determine whether an R wave has been detected at the right ventricle. If an R wave or electrical activation has been detected at the right ventricle, the processor then in step 123 determines the time (T) since the first timer 64 was last reset and stores that time interval in the memory 92. The processor then returns to step 120 to reset the first timer 64.

If in step 124 the processor had determined that the first timer 64 had expired, it would proceed to step 126 to pace the right ventricle. In so doing, the microprocessor activates the pacer output 108 and causes the pacer output 108 to provide an electrical stimulating pulse to the electrodes 38 and 40 of the first lead 34. The timeout time of the first timer 64 may be, for example, one second and may be programmed into the memory 92 through the external controller 100 and the receiver/transmitter 102.

Upon the pacing of the right ventricle in step 126, the processor then in step 128 determines the time on the first timer 64 and stores that time as a determined time interval. The processor then returns to step 120 to once again reset the first timer.

As can thus be seen, the atrial defibrillator 30 provides bradycardia pacing of the right ventricle 12 and, upon each electrical activation being sensed at the right ventricle, determines the time interval since the first timer 64 was reset by either a sensed electrical activation of the right ventricle or a stimulating pulse being delivered to the right ventricle during bradycardia pacing. Hence, in determining the time intervals, the sensed electrical activations of the right ventricle and the delivery of a stimulating pacing pulse to the right ventricle are considered to be equivalent events in that each results in a depolarization of the right ventricle.

Figure 3:
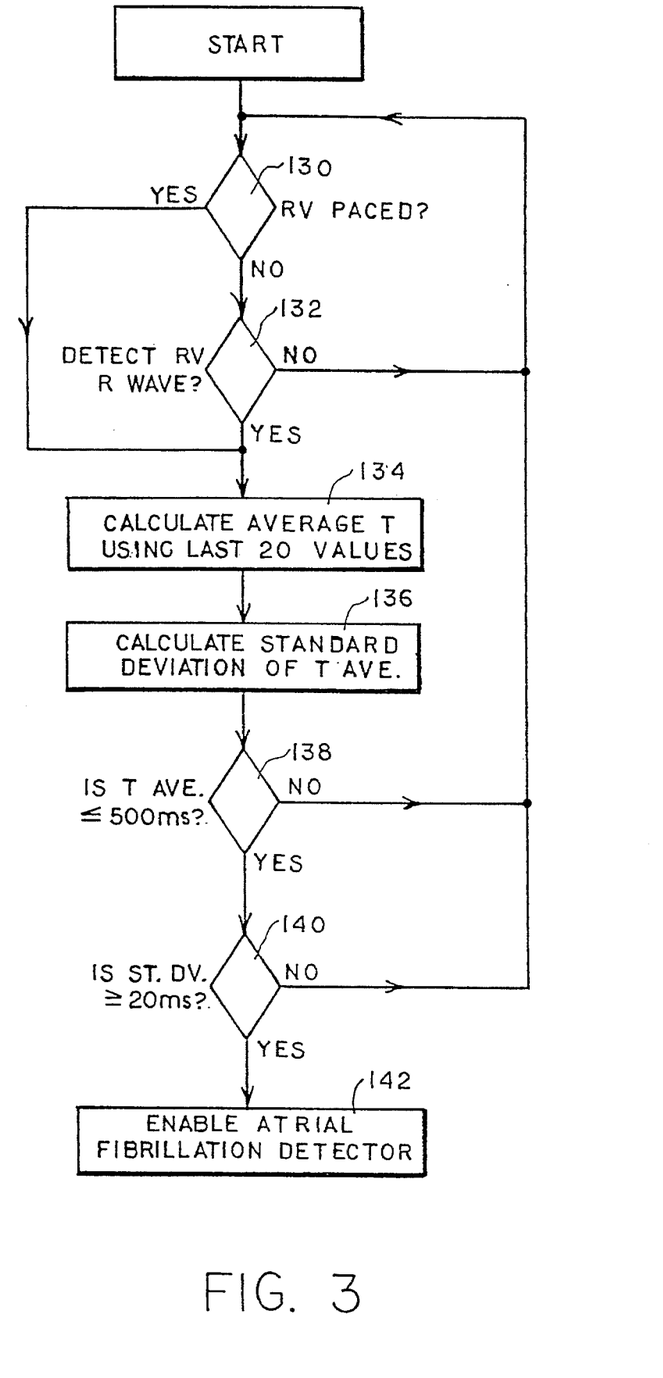
FIG. 3 is a flow diagram illustrating the manner in which the atrial defibrillator of FIG. 1 may be implemented in accordance with the present invention for enabling the atrial fibrillation detector of the atrial defibrillator.

Referring now to FIG. 3, it illustrates the manner in which the atrial defibrillator 30 may be implemented for enabling the atrial fibrillation detector 82. This process begins at step 130 wherein the microprocessor first determines whether the right ventricle has been paced by the pacer output 108. If the right ventricle has not been paced, the processor proceeds to step 132 to determine whether an R wave has been detected at the right ventricle. If an R wave has not been detected at the right ventricle, the processor returns to step 130 to once again determine whether the right ventricle has been paced. If the right ventricle has been paced as determined in step 130, or if an R wave has been detected at the right ventricle in step 132, the processor then proceeds to step 134 to calculate an average time interval using the last twenty stored time interval values. This is performed by the average calculation stage 74 of the microprocessor 62.

After calculating the average time interval over the last twenty stored values of the time interval, the processor then proceeds to step 136 to calculate the standard deviation of the average time interval calculated in step 134 for the last twenty stored values of the time interval. The standard deviation is calculated in the standard deviation calculation stage 76.

After calculating both the average time interval for the last twenty stored values of the time interval and the standard deviation for the average time interval for the last twenty stored values of the time interval, the processor then proceeds to step 138 to determine if the average time interval calculated in step 134 is less than or equal to a first predetermined time interval of, for example, 500 milliseconds. If the average time interval calculated in step 134 is not less than or equal to 500 milliseconds, the processor then returns to step 130 to once again determine whether the right ventricle has been paced.

If in step 138 the processor determines that the average time interval calculated in step 134 is less than or equal to 500 milliseconds, the processor then proceeds to step 140 to determine if the standard deviation calculated in step 136 is greater than or equal to a predetermined standard deviation of, for example, twenty milliseconds. If the standard deviation calculated in step 136 is not greater than or equal to twenty milliseconds, the processor returns to step 130 to once again determine whether the right ventricle has been paced. However, if the standard deviation calculated in step 136 is greater than or equal to the predetermined standard deviation of, for example, twenty milliseconds, the processor then proceeds to step 142 to enable the atrial fibrillation detector. This step is performed through the enable stage 78 which enables the atrial fibrillation detector 82, the analog-to-digital convertor 60, and the third sense amplifier 54 over a control line 55. This causes the atrial fibrillation detector 82, the analog-to-digital convertor 60, and the third sense amplifier 54 to be activated.

As can thus be seen by the implementation illustrated in FIG. 3, the atrial defibrillator 30 activates the atrial fibrillation detector 82, the analog-to-digital convertor 60, and the third sense amplifier 54 responsive to the determined time intervals, and preferably, the last twenty time intervals stored in the memory 92. This allows the atrial fibrillation detector 82, the analog-to-digital convertor 60, and the third sense amplifier 54 to be normally disabled to avoid excessive consumption of the battery 114. This is particularly important because the algorithms utilized in arrythmia detectors, such as fibrillation detectors, consume considerable power and, if left continuously energized, would require frequent replacement of the defibrillators in which they are employed for the purpose of replacing the depletable power sources, such as a battery.

The criteria utilized for activating the atrial fibrillation detector is both the average heart rate and the variability of the heart rate. By utilizing this criteria, the atrial fibrillation detector need only be activated when there is a probability that atrial fibrillation is present to thus permit the atrial fibrillation detector, the analog-to-digital convertor 60, and the third sense amplifier 54 to be normally disabled for conserving the power of the depletable power source.

Thus far, it will also be noted that only the right ventricle is being sensed, Only electrical activations of the right ventricle are sensed for either providing bradycardia pacing of the right ventricle or for enabling the atrial fibrillation detector. This assures that little power is consumed during the times in which neither bradycardia pacing is required or in which there is a low probability that atrial fibrillation is present in the heart.

In accordance with the present invention, the atrial fibrillation detector 82, the analog-to-digital convertor 60, and the third sense amplifier 54 may also be activated manually from external to the patient's skin. This external activation may be accomplished by, for example, the patient's physician sending suitable commands from the external controller 100. The commands would then be received by the receiver/transmitter 102 and conveyed to the microprocessor 62 which would then, in response to the received command, activate the atrial fibrillation detector 82, the analog-to-digital convertor 60, and the third sense amplifier 54.

Figure 4:
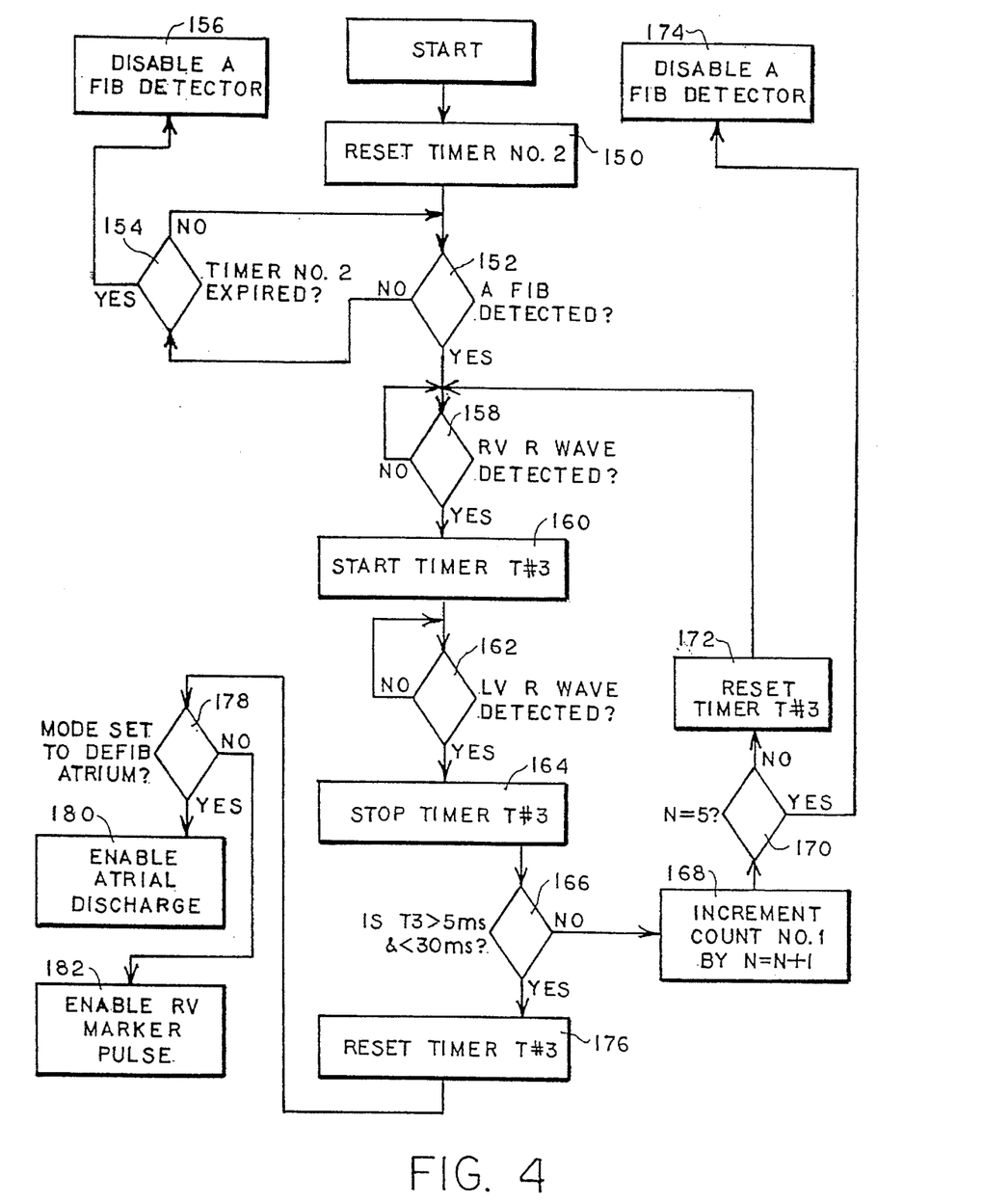
FIG. 4 is a flow diagram illustrating the manner in which the atrial defibrillator of FIG. 1 may be implemented in accordance with the present invention for detecting atrial fibrillation and enabling either the atrial defibrillating output or the right ventricle marker pulse output.

Referring now to FIG. 4, it illustrates the manner in which the atrial defibrillator 30 may be implemented for detecting the occurrence of atrial fibrillation in the heart and for enabling either the atrial defibrillation output or the right ventricle marker output of the atrial defibrillator.

This process begins at step 150 wherein the microprocessor resets the second timer 66. The processor then proceeds to step 152 to determine whether atrial fibrillation is detected. Here it is assumed that the average time interval calculated in step 134 for the last twenty values of the stored time intervals was less than or equal to 500 milliseconds, and that the standard deviation of the average time interval for the last twenty stored values of the time intervals was greater than twenty milliseconds as calculated in step 136 and determined in step 140 to cause the atrial fibrillation detector 82, the analog-to-digital convertor 60, and the third sense amplifier 54 to be activated by the control line 55. Atrial fibrillation may be detected by the microprocessor through processing the digitized values of the atrial activity provided by the analog-to-digital convertor 60. As previously mentioned, the atrial activity is sensed by the second electrode 44 and third electrode 46 of the second lead 36 and the third sense amplifier 54.

There are many algorithms known in the art for processing such data to determine if fibrillation is present. One such algorithm is disclosed in a paper: Nitish V. Thakor, Yi-Sheng Zhu and Kong-Yan Pan, "Ventricular Tachycardia and Fibrillation Detection by a Sequential Hypothesis Testing Algorithm," *IEEE Transactions On Biomedical Engineering*," Vol. 37, No. 9, pp. 837–843, September 1990. Implementing such an algorithm by a microprocessor such as microprocessor 62 is well within the preview of one skilled in the art.

If in step 152 it is determined that atrial fibrillation is not currently taking place in the heart, the microprocessor then proceeds to step 154 to determine whether the second timer 66 has expired. If the second timer has not expired, the processor returns to step 152 to again determine whether atrial fibrillation is currently taking place in the heart. If in step 154 it is determined that the second timer 66 has expired, the processor then proceeds to step 156 to disable the atrial fibrillation detector. This step is performed after a predetermined expiration time of the timer 66, which may be, for example, six seconds.

If the atrial defibrillator in step 152 determines that atrial fibrillation is currently present in the heart, the microprocessor then proceeds to determine whether it is able to obtain a reliable synchronizing pulse for synchronizing the delivery of the defibrillating or cardioverting electrical energy to the atria. This begins in step 158 where the atrial defibrillator microprocessor determines whether an electrical activation has been detected in the right ventricle. If an R wave has not been detected in the right ventricle, the microprocessor performs a loop to once again determine at step 158 if an R wave has been detected in the right ventricle. When an R wave is detected in the right ventricle, the microprocessor proceeds to step 160 to start the third timer 68. After starting timer 68, the processor then proceeds to step 162 to determine whether an R wave has been detected in the left ventricle. If an electrical activation has not been detected at the left ventricle, the microprocessor then returns to step 162 to once again determine whether an R wave has been detected at the left ventricle. When an R wave is detected at the left ventricle, the microprocessor then proceeds to step 164 to stop the third timer 68. In so doing, the third timer 68 will have the time from when the R wave was detected at the right ventricle in step 158 and when the same R wave was detected at the left ventricle in step 162.

The microprocessor then proceeds to step 166 to determine if the time between the detection of the electrical activation at the right ventricle and at the left ventricle is within a range of normal delay times between depolarization activation waves being sensed at the right ventricle and the left ventricle. The predetermined range may be established by programming the range into the memory 92 from the external controller, through the receiver/transmitter 102 and the microprocessor 62. The normal delay times may, for example, range from five milliseconds to thirty milliseconds. As a result, in step 166, the microprocessor determines whether the time between the sensing of the electrical activation and the right ventricle and in the left ventricle was greater than five milliseconds and less then thirty milliseconds. If it was not, this is considered to be a negative test resulting in an unreliable synchronizing detection. In this event, the microprocessor proceeds to step 168 to increment the first counter 84. The microprocessor then proceeds to step 170 to determine whether the count in the first counter 84 is equal to a predetermined count of, for example, five. If it is not, the processor then resets the third timer 68 in step 172 and returns to step 158 to detect another R wave at the right ventricle for detecting whether a reliable synchronizing pulse may be detected. When the count within the first counter 84 reaches the predetermined count of five, the processor then proceeds to step 174 to disable the atrial fibrillation detector 82. Both this step and step 156 may be performed by the disable stage 80 providing a disable signal over the control line 55 for disabling the atrial fibrillation detector, the analog-to-digital convertor 60, and the third sense amplifier 54.

As can be seen from the foregoing, the atrial defibrillator will go no further in its processing even though atrial fibrillation has been detected if it is not assured that a reliable synchronization pulse could be generated for synchronizing the delivery of the defibrillating or cardioverting electrical energy to the atria in synchronism with an electrical activation of the heart. This also, as will be seen hereinafter, negates the need for activating the charging circuit 110 for charging the storage capacitor if a defibrillating pulse could not be reliably applied in synchronism with an electrical activation of the heart to further conserve the depletable power source of the battery 114.

In determining whether a reliable synchronization pulse can be derived, and as will be seen hereinafter, in providing a synchronization pulse, the atrial defibrillator first senses a depolarization activation wave at a first area of the heart and senses the same depolarization activation wave at a second area of the heart. In accordance with this preferred embodiment, the first area of the heart is the right ventricle and the second area of the heart is the left ventricle. If the activation wave at the right and left ventricle is detected coincidently, as will be determined in step 166, or detected at times too far apart to be considered a legitimate electrical activation wave, a synchronization pulse will not be derived nor will such detection be considered a positive test of the ability to derive such a synchronization pulse. The foregoing is based upon the fact that electrical activation depolarization waves propagate across the heart so that the sensing of an electrical activation at two different areas of the heart should occur at different times while noise, which may be mistaken for an electrical activation, would be detected at both areas of the heart simultaneously. As a result, the non-coincident sensing of an electrical activation at two different areas of the heart such as at the right ventricle and the left ventricle provide a reliable indication that the sensed electrical activation is a real or legitimate electrical activation and can be relied upon for deriving a reliable synchronization pulse for synchronizing the delivery of a defibrillating or cardioverting electrical pulse to the atria in synchronism with an electrical activation of the heart.

Referring again to FIG. 4, if in step 166 it is determined that there has been non-coincident sensing of an electrical activation at the right ventricle and the left ventricle by determining that such sensing occurred within a time greater than five milliseconds and less than thirty milliseconds, the microprocessor proceeds to step 176 to reset the third timer 68. After resetting timer 68, the microprocessor then determines in step 178 if the atrial defibrillator is set in the defibrillating mode. In performing this step, the microprocessor accesses the contents of a known storage location in the mode selection portion 98 of memory 92 to determine, for example, if that bit is set or not set. For example, if the bit is set this may be considered by the microprocessor as indicating that the atrial defibrillator is set in the defibrillating mode. If the bit is not set, the microprocessor may consider this as indicating that the atrial defibrillator is in the right ventricle marker mode and not the atrial defibrillating mode. Hence, if it is determined in step 178 that the atrial defibrillator is in the atrial defibrillating mode, it will then in step 180 enable the charge delivery and energy control stage 90. If the atrial defibrillator is not in the atrial defibrillating mode, the microprocessor will then enable the sync marker controller 70 in step 182.

Figure 5:
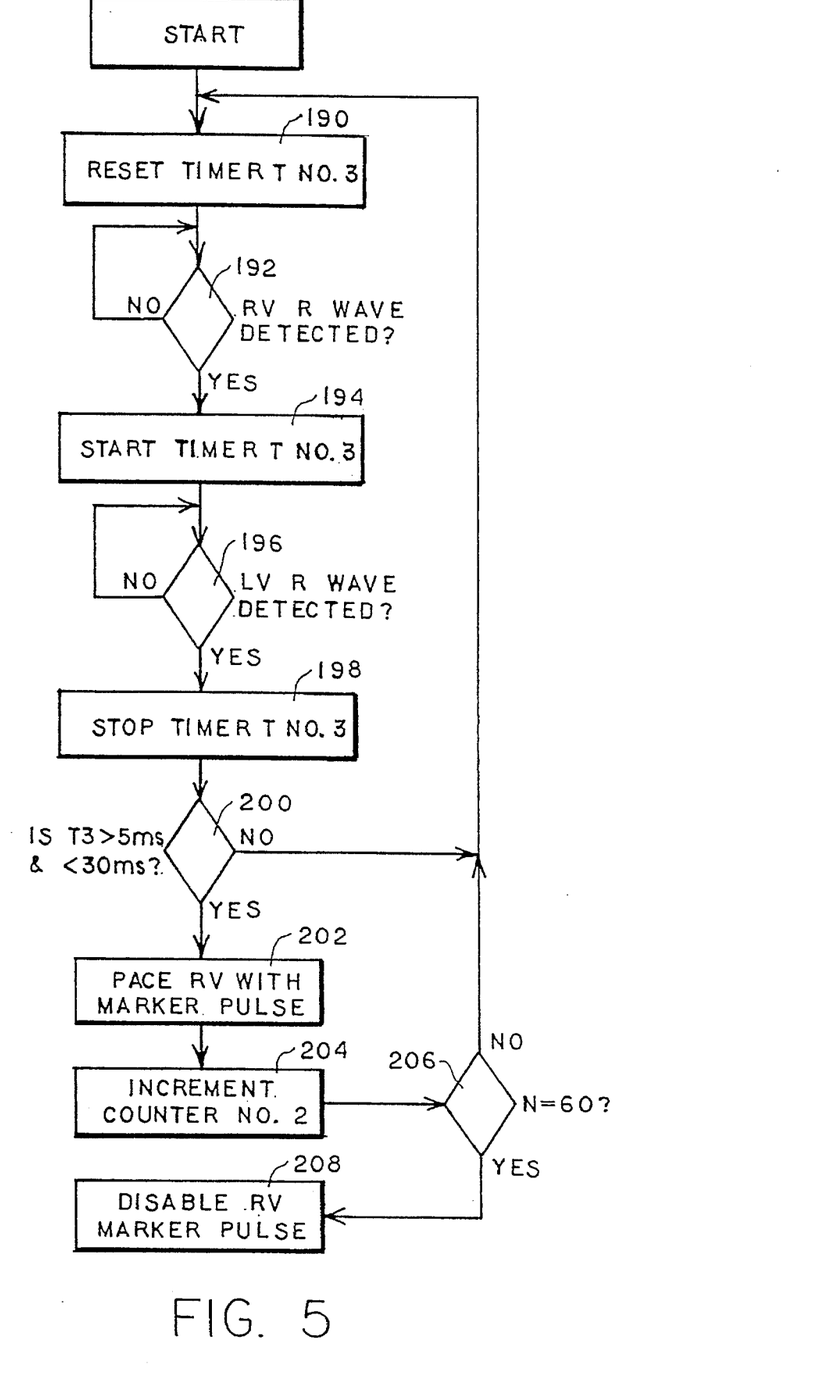
FIG. 5 is a flow diagram illustrating the manner in which the atrial defibrillator of FIG. 1 may be implemented for providing right ventricle marker pulses in synchronism with detected electrical activations (R waves) of the heart.

Referring now to FIG. 5, it illustrates the manner in which the atrial defibrillator 30 may be implemented for providing marker sync pulses to the right ventricle 12 of the heart 10. The foregoing assumes that in step 178, the microprocessor determined that the atrial defibrillator was in the marker pulse mode and has enabled the sync marker controller 70.

This process begins at step 190 with the microprocessor resetting the third timer 68. The microprocessor then proceeds to step 192 to determine whether an R wave has been detected at the right ventricle. If an R wave has not been detected, the microprocessor continues to determine whether an R wave has been detected at the right ventricle until an R wave is detected. When an R wave is detected at the right ventricle, the microprocessor then proceeds to step 194 to start the third timer 68. It then advances to step 196 to determine whether the R wave has been detected at the left ventricle. If the R wave has not been detected at the left ventricle, the microprocessor continues to determine whether an R wave has been detected at the left ventricle and when the R wave has been detected at the left ventricle, the microprocessor then at step 198 stops the third timer 68. After stopping timer 68, the microprocessor then proceeds to step 200 to determine if the time between the sensing of the R wave at the right ventricle and at the left ventricle occurred within a time greater than five milliseconds and less than thirty milliseconds. If it has not, the detected R wave is considered to be either noise or an unreliable detection and the microprocessor returns to step 190 to reset the third timer 68. If, however, the microprocessor determines in step 200 that the R wave was detected at the right ventricle and the left ventricle within the normal delay time range of five milliseconds and thirty milliseconds, the microprocessor then proceeds to step 202 to pace the right ventricle with a marker pulse. This step is performed by the sync detector 72 providing a sync pulse to the sync marker controller 70 and the sync marker controller 70 causing the pacer output 108 to pace the right ventricle.

After the right ventricle is paced with the marker pulse, the microprocessor proceeds to step 204 to increment the second counter 86. The microprocessor then proceeds to step 206 to determine whether the second counter 86 has reached a predetermined count of, for example, sixty marker pulses. If it has not, the microprocessor returns to step 190 to reset the third timer 68 and to detect another electrical activation of the heart for providing a synchronizing pulse. If the count in the second counter 86 has reached the predetermined number of marker pulses counted, such as sixty pulses, the microprocessor then proceeds to step 208 to disable the sync marker controller 70 and to terminate the provision of the marker pulses to the right ventricle.

As can be seen by the foregoing, the atrial defibrillator 30 is arranged to provide marker pulses to enable a physician to determine whether proper operating parameters have been established within the atrial defibrillator for reliably detecting electrical activations to provide reliable synchronizing pulses. The marker pulses provided to the right ventricle are preferably of a relatively low energy, and of an energy which is insufficient to cardiovert or defibrillate the heart, but which may be sufficient for pacing the right ventricle of the heart. For example, the quantity of electrical energy utilized in each marker pulse may have an energy in the range of five to fifty microjoules and preferably twenty-five microjoules. Marker pulse energies of, for example, twentyfive microjoules, although being sufficient to pace the right ventricle of the heart, would not adversely affect normal heart rhythm, inasmuch as the marker pulses are being provided in synchronism with detected electrical activations of the heart and, more particularly, reliably detected activations of the heart in accordance with the present invention. The marker pulses, if applied in the range of energies noted above, will have energies sufficient so as to be detected on an electrocardiogram generated externally to the skin of the patient by a physician in a known manner.

Figure 6:
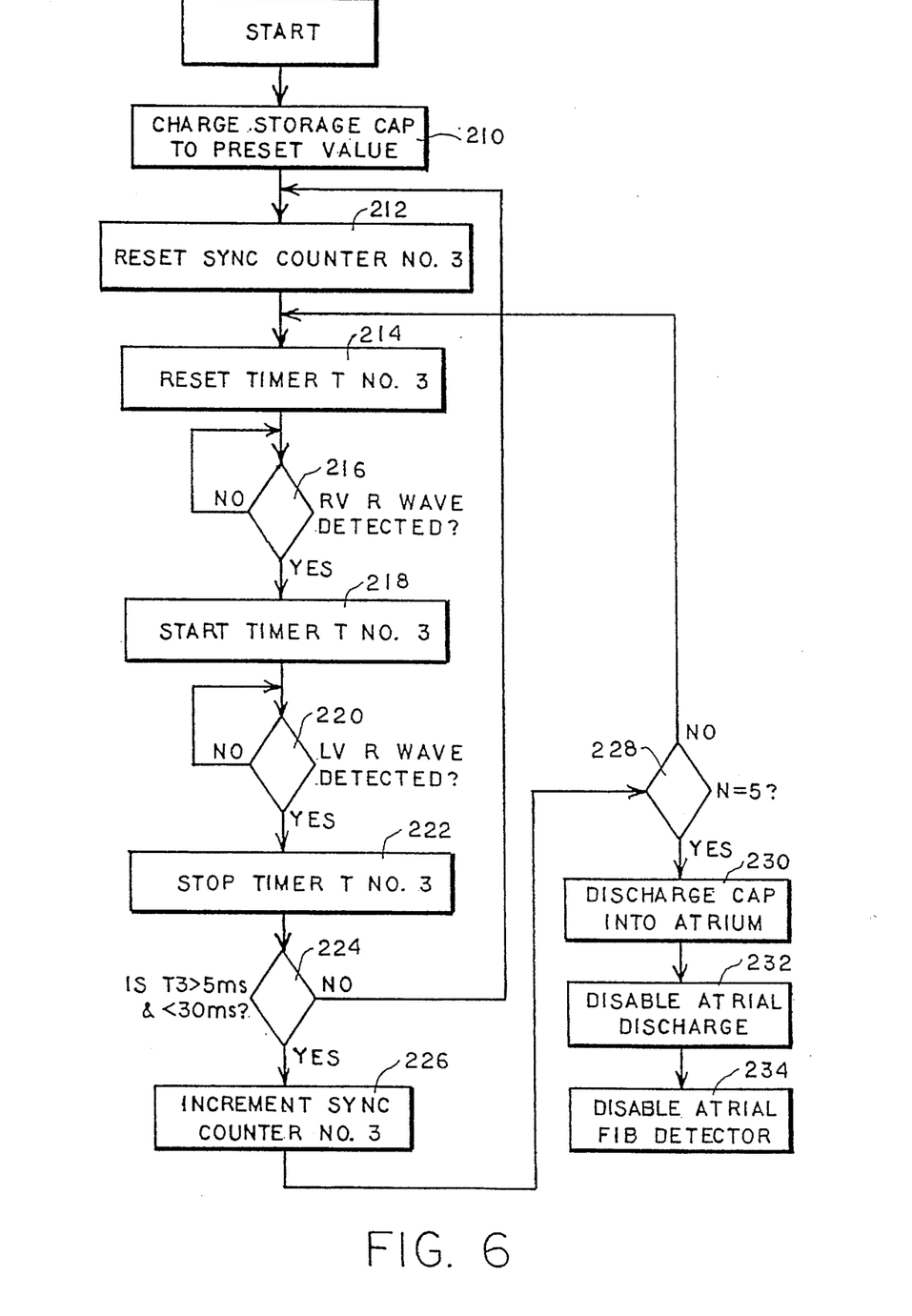
FIG. 6 is a flow diagram illustrating the manner in which the atrial defibrillator of FIG. 1 may be implemented for providing defibrillating electrical energy to the atria of the heart in synchronism with detected electrical activations (R waves) of the heart.

Referring now to FIG. 6, it illustrates the manner in which the atrial defibrillator 30 may be implemented for applying cardioverting or defibrillating energy to the atria 16 and 18 of the heart 10. For this description, it is assumed that in step 178 the microprocessor determined that the atrial defibrillator was in the atrial defibrillating mode and that the charge delivery and energy control stage 90 had been activated by the microprocessor.

This process begins at step 210 with the charge delivery and energy control stage 90 providing over control line 111 an enable signal to enable the charger to charge the storage capacitor of the charger and storage capacitor circuit 110. The microprocessor then proceeds to step 212 to reset the third counter 88 which, as will be seen hereinafter, is utilized to count synchronizing pulses. The processor then proceeds to step 214 to reset the third timer 68. After resetting the third timer 68, the processor proceeds to step 216 to determine whether an R wave has been detected at the right ventricle. If an R wave has not been detected at the right ventricle, the microprocessor continues to determine whether an R wave has been detected at the right ventricle and when one is detected, the microprocessor proceeds to step 218 to start the third timer 68. After starting the third timer 68, the microprocessor proceeds to step 220 to determine whether the R wave has been detected at the left ventricle. If the R wave has not been detected at the left ventricle, the processor continues to determine whether the R wave has been detected at the left ventricle and when it is detected, the microprocessor in step 222 stops the third timer 68. After stopping the third timer 68, the microprocessor then in step 224 determines whether the detection of the R wave at the right ventricle and at the left ventricle occurred within the normal range of delay times of five milliseconds to thirty milliseconds. If it had not been so detected, the microprocessor then returns to step 212 to reset the third counter 88. If the R wave had been detected at the right ventricle and the left ventricle within the normal delay time, the microprocessor then proceeds to step 226 to increment the third counter 88. After incrementing the third counter 88, the microprocessor determines in step 228 if the third counter has reached a count of five. If it has not, the microprocessor returns to step 214 to once again reset the third timer 68 for detecting another electrical activation of the heart. When the third counter reaches a predetermined count of, for example, five counts, the microprocessor then proceeds to step 230 for discharging the capacitor of circuit 110. The discharging of the capacitor is controlled by the discharge circuit 112 and the discharge duration is determined by a signal carried on a control line 113 to control the duration of the discharge and thus the quantity of electrical energy delivered to the atria of the heart. The defibrillating or cardioverting energy is delivered between the second electrode 44 and the third electrode 46 of the second lead 36 to confine the cardioverting or defibrillating energy to the atria of the heart. The quantity of energy delivered to the atria for cardioverting or defibrillating the atria may be in the range of 0.1 to 3 joules. The actual quantity of defibrillating energy required will vary from patient to patient but, in the majority of the cases, will fall within the range of 0.1 to 3 joules.

After applying the defibrillating energy to the atria of the heart, the microprocessor then proceeds to step 232 to disable the charge delivery and energy control stage 90. Lastly, the microprocessor then proceeds to step 234 to disable the atrial fibrillation detector 82.

From the foregoing, it can be seen that five consecutive reliable synchronizing pulses must be provided by the sync detector 72 before defibrillating or cardioverting electrical energy is applied to the atria of the heart to assure reliable synchronization. Upon the fifth synchronizing pulse, the defibrillating or cardioverting electrical energy is then applied to the atria of the heart which will occur in synchronism with the last one of the predetermined number of electrical activations detected by the sync detector 72. As a result, reliable synchronization of the defibrillating or cardioverting electrical energy with a detected electrical activation of the heart will be assured.

Once the atrial fibrillation detector is disabled in step 234, the atrial defibrillator returns to once again determine the probability of atrial fibrillation and, if there is a probability of atrial fibrillation, to once again enable the atrial fibrillation detector. This begins the implementation of the atrial defibrillator, as illustrated in the flow diagrams of FIGS. 4–6.

Figure 7:
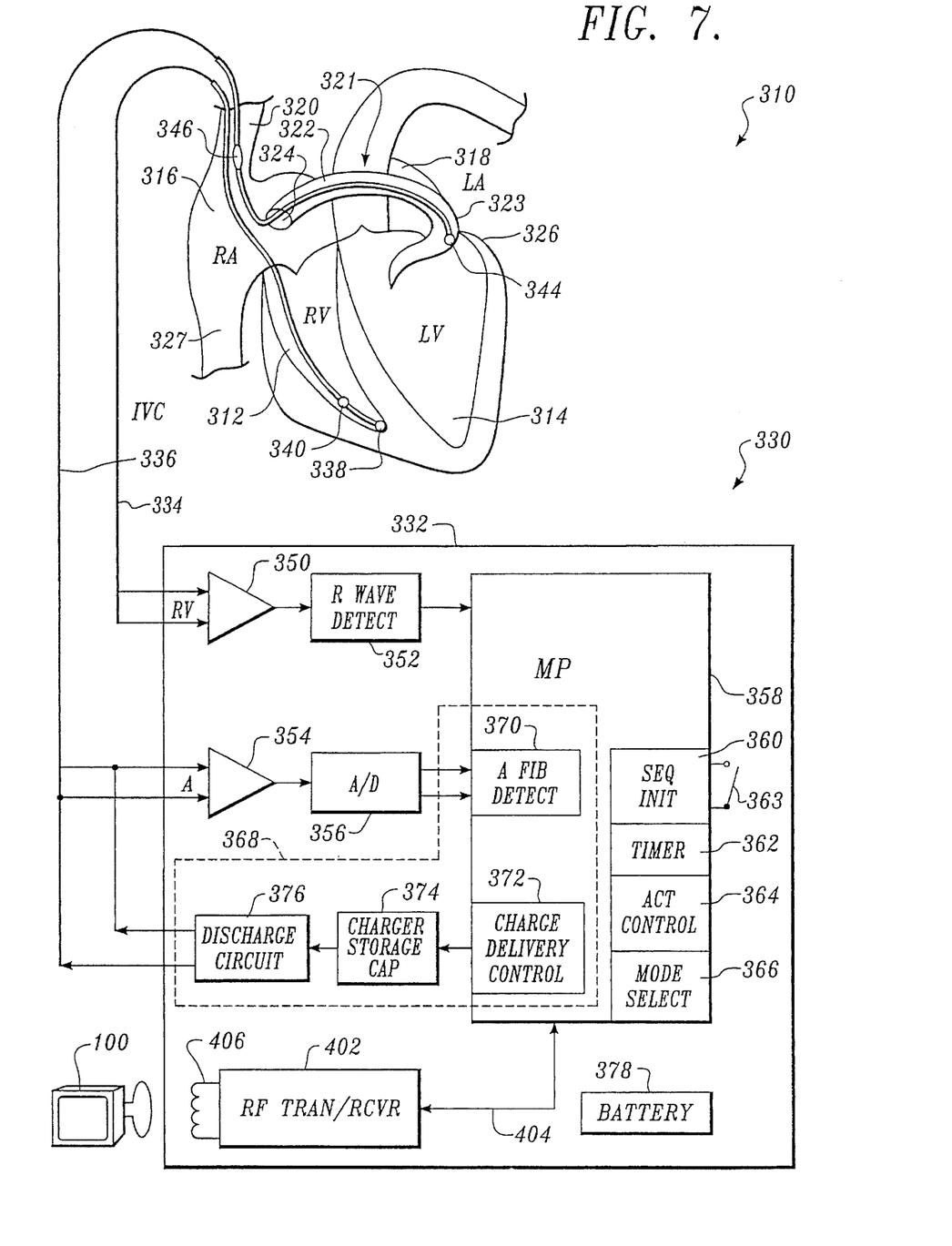
FIG. 7 is a schematic block diagram of another fully implantable atrial defibrillator embodying the present invention for applying defibrillating electrical energy to the atria of a human heart and which is shown in association with a human heart in need of atrial fibrillation monitoring and potential cardioversion of the atria.

Referring now to FIG. 7, it illustrates another fully implantable atrial defibrillator 330 embodying the present invention shown in association with a schematically illustrated human heart 310 in need of atrial fibrillation monitoring-and potential cardioversion of the atria. The portions of the heart 310 illustrated in FIG. 7 are the right ventricle 312, the left ventricle 314, the right atrium 316, the left atrium 318, the superior vena cava 320, the coronary sinus channel 321 which, as used herein, denotes the coronary sinus 322 and the great cardiac vein 323, the coronary sinus ostium or opening 324, the left ventricular free wall 326 and the inferior vena cava 327.

The atrial defibrillator 330 generally includes an enclosure 332 for hermetically sealing the internal circuit elements of the atrial defibrillator to be described hereinafter, an endocardial first lead 334, and an intravascular second lead 336. The enclosure 332 and first and second leads 334 and 336 are arranged to be implanted beneath the skin of a patient so as to render the atrial defibrillator 330 fully implantable.

The endocardial first lead 334 preferably comprises a endocardial bi-polar lead having electrodes 338 and 340 arranged for establishing electrical contact with the right ventricle 312 of the heart 310. The electrodes 338 and 340 permit bi-polar sensing of ventricular activations in the right ventricle. As illustrated, the lead 334 is preferably fed through the superior vena cava 320, into the right atrium 316 and then into the right ventricle 312, as illustrated.

The second lead 336 generally includes a first or tip electrode 344 and a second or proximal electrode 346. As illustrated, the second lead 336 is flexible and arranged to be passed down the superior vena cava 320, into the right atrium 316, into the coronary sinus ostium 324, and advanced into the coronary sinus channel 321 of the heart near the left side thereof so that the first or tip electrode 344 is within the coronary sinus channel 321 either within the coronary sinus 322 adjacent the left ventricle 314 and beneath the left atrium 318 or most preferably within the great cardiac vein 323 adjacent the left ventricle 14 and beneath the left atrium 318. The electrodes 344 and 346 are spaced apart such that when the first electrode 344 is positioned as described above, the second electrode 346 is in the right atrium 316.

The first electrode 344 together with the second electrode 346 provide bi-polar sensing of heart activity in the atria 316 and 318. The first electrode 344 and the second electrode 346 further provide for the delivery of defibrillating or cardioverting electrical energy to the atria.

Within the enclosure 332, the atrial defibrillator 330 includes a first sense amplifier 350, an R wave detector 352, and a second sense amplifier 354. The first sense amplifier 350 and the R wave detector 352, together with electrodes 338 and 340 of lead 334, sense ventricular activations of the right ventricle 312. The second sense amplifier 354, together with the first electrode 344 and second electrode 346 of the second lead 336, detect atrial activity of the heart.

The output of the first sense amplifier 350 is coupled to the R wave detector 352. The R wave detector 352 is of the type well known in the art which provides an output pulse upon the occurrence of an R wave being sensed during a cardiac cycle of the heart. The output of the second sense amplifier 354 is coupled to an analog-to-digital convertor 356 which converts the analog signal representative of the atrial activity of the heart being detected to digital samples for further processing in a manner to be described hereinafter.

The enclosure 332 of the atrial defibrillator 330 further includes a microprocessor 358. The microprocessor 358 is preferably implemented in a manner as previously descried or as described in copending U.S. application Ser. No. 07/856,514, and further as described hereinafter with respect to the flow diagram of FIG. 8. The implementation of the microprocessor 358 in accordance with this embodiment of the present invention results in a plurality of functional stages. The stages include a sequence initiating stage 360, a timer 362, an activation control stage 364, a mode select stage 366, an atrial fibrillation detector 370, and a charge and delivery control stage 372.

The microprocessor 358 is arranged to operate in conjunction with a memory (not shown) which may be coupled to the microprocessor 358 by a multiple-bit address bus (not shown) and a bi-directional multiple-bit data bus (not shown). This permits the microprocessor 358 to address desired memory locations within the memory for executing write or read operations. During a write operation, the microprocessor stores data and operating parameters (such as a selected modality) in the memory at the addresses defined by multiple-bit addresses conveyed over the address bus and conveys the data to the memory over the multiple-bit data bus. During a read operation, the microprocessor 358 obtains data from the memory at the storage locations identified by the multiple-bit addresses provided over the address bus and receives the data from the memory over the bi-directional data bus.

For entering operating parameters into the microprocessor 358, such as mode selection, the microprocessor 358 receives programmable operating parameters, such as mode commands, from an external controller 400 which is external to the skin of the patient. The external controller 400 is arranged to communicate with a receiver/transmitter 402 which is coupled to the microprocessor 358 over a bi-directional bus 404. The receiver/transmitter 402 may be of the type well known in the art for conveying various information which it obtains from the microprocessor 358 to the external controller 400 or for receiving programming parameters, such as mode commands, from the external controller 400 which the receiver/transmitter 402 then conveys to the microprocessor 358 for storage in the aforementioned external memory within enclosure 332.

The receiver/transmitter 402 includes a transmitting coil 406 so that the receiver/transmitter 402 and coil 406 form a communication means. Such communication means are well known in the art and may be utilized as noted above for receiving commands from external to the implantable enclosure 332 and for transmitting data to the external controller 400 from the implanted enclosure 332. One such communication system is disclosed, for example, in U.S. Pat. No. 5,342,408, which is incorporated herein by reference.

The atrial defibrillator 330 further includes an intervention sequencer 368 which performs an intervention sequence, including atrial fibrillation detection and cardioversion of the atria (if necessary). To that end, the intervention sequencer includes the previously mentioned atrial fibrillation detector 370 and charge and delivery control 372, and a charger and storage capacitor circuit 374 and a discharge circuit 376.

Each intervention sequence is begun by the sequence initiating stage 360. As will be seen hereinafter, when the defibrillator 330 is programmed in the automatic mode, the sequence initiating stage 360 initiates an intervention sequence at spaced apart times which are preferably determined by the timer 362. When the defibrillator is programmed in the patient activated mode, the sequence initiating stage 360 initiates an intervention sequence when a sequence command generated external to the patient is received by a sequence command receiver, preferably formed by a read switch 363. The sequence command, in accordance with this preferred embodiment, is a magnetic field generated by a magnet of the type well now in the art which is brought into close proximity with the implanted defibrillator 330. When the intervention sequencer 368 is not performing an intervention sequence, it is held in a deactivated or inactive state by the activation control stage 364. When an intervention sequence is to be performed, the sequence initiating stage 360 overrides the activation control stage 364 to cause the intervention sequencer to perform an intervention sequence.

Each intervention sequence preferably begins with the atrial fibrillation detector 370 determining if the atria are in need of cardioversion. This analysis is preferably performed on data obtained from sense amplifier 354 and analog-to-digital convertor 356, which is prestored in the aforementioned memory (not shown) external to the microprocessor 358, but contained within the implantable enclosure 332. The atrial fibrillation detector 370 may alternatively be of the type which performs real time analysis of the data provided by the analog-to-digital convertor 356.

If the atria are in fibrillation, and hence in need of cardioversion, the charger and storage capacitor circuit 374 under control of the charge and delivery stage 372 charges its storage capacitor to a predetermined voltage level for cardioverting the atria of the patient's heart. When the capacitor of circuit 374 is charged, the charge and delivery control stage 372 then causes the discharge circuit 376 to discharge the storage capacitor within circuit 374 for a predetermined time to provide a controlled discharge of cardioverting electrical energy to the atria of the heart. To that end, the discharge circuit 376 is coupled to the first electrode 344 and the second electrode 346 of the second lead 336 for applying the cardioverting or defibrillating electrical energy to the atria. The discharge is preferably initiated in timed relation to an R wave detected by sense amplifier 350 and R wave detector 352. Interval timing prior to energy delivery is also preferably performed as taught in U.S. Pat. No. 5,207,219.

Lastly, the defibrillator 330 includes a depletable power source 378, such as a lithium battery. The battery 378, of course, provides power to the electrical components of the atrial defibrillator 330.

Figure 8:
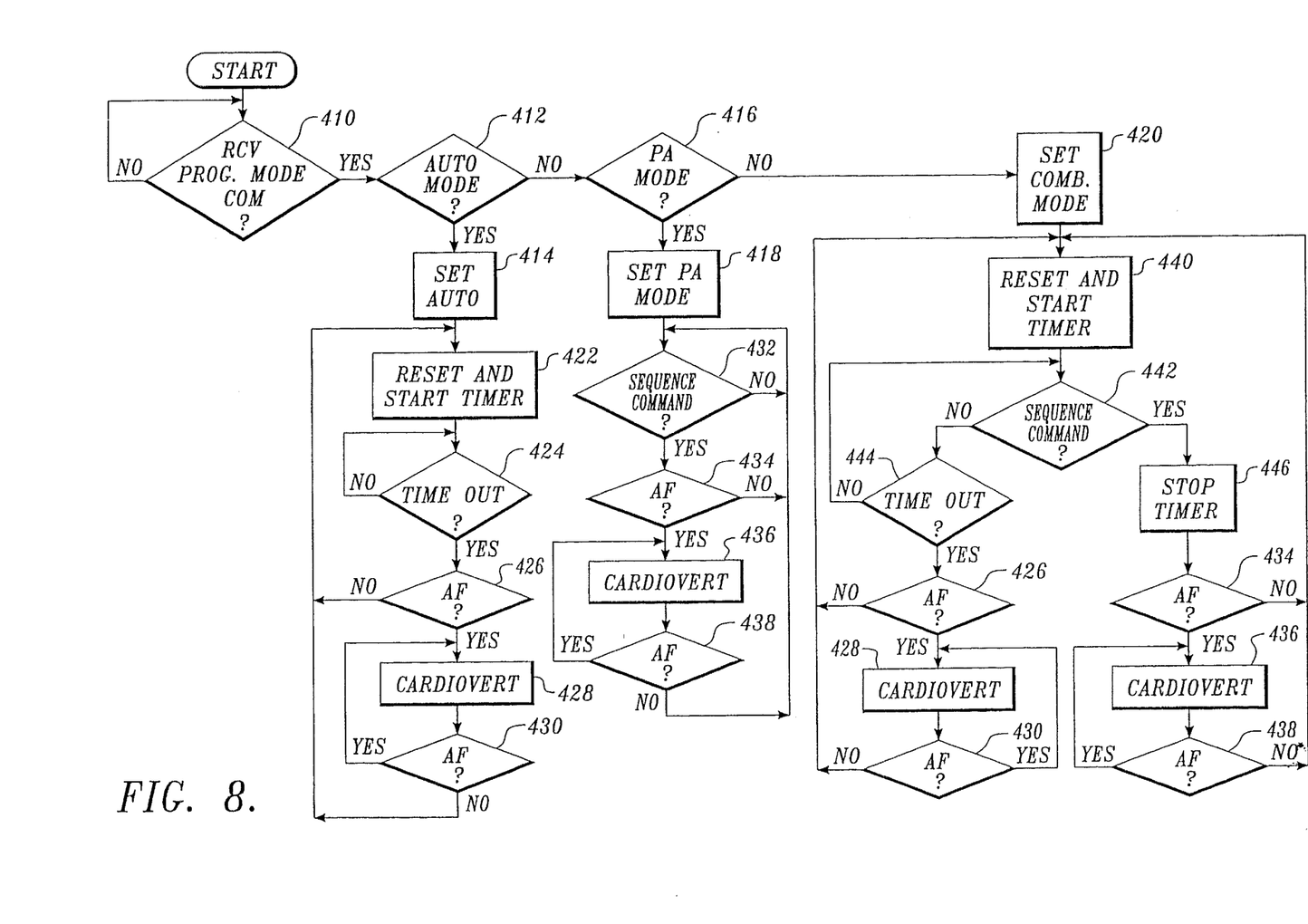
FIG. 8 is a flow diagram illustrating the manner in which the atrial defibrillator of FIG. 7 may be implemented for providing a patient activated modality, a fully automatic modality, or a combined patient activated and fully automatic modality in accordance with the present invention.

The overall operation of the atrial defibrillator 330 will now be described in connection with the flow diagram of FIG. 8. Referring now to FIG. 8, the atrial defibrillator 330 is first placed into one of a plurality of different modes of operation. In accordance with this preferred embodiment, the selectable modalities include an automatic mode, a patient activated mode, and a combined automatic and patient activated mode. To that end, at relatively short, predetermined time intervals, the RF transmitter/receiver 402 is activated to determine if the external controller 400 is attempting to communicate with the implanted defibrillator 330. As a result, in accordance with step 410, the mode select stage 366, when the external controller 400 is transmitting to the transmitter/receiver 402, will determine if a program mode command is being received from the external controller 400. If a program mode control is being received, the mode select stage 366 will decode the mode command and set the defibrillator 330 into the selected mode of operation.

The mode select stage 366 first determines in step 412 if the received program mode command corresponds to the automatic mode. If it does, it then proceeds to step 414 to set the microprocessor 358 into the automatic mode for obtaining those programs instructions from the external memory which correspond to the automatic mode of operation, to be described subsequently.

If in step 412 it is determined that the received program mode command does not correspond to the automatic mode, the mode select stage 366 then proceeds to step 416 to determine if the received program mode command corresponds to the patient activated mode. If it does, the mode select stage 366 then in step 418 sets the microprocessor into the patient activated mode for obtaining those operating instructions from the external memory which correspond to the patient activated mode, to be described subsequently.

If in step 416, the mode select stage 366 determines in step 416 that the received program mode command does not correspond to the patient activated mode, it then proceeds to step 420 to set the microprocessor into the combined automatic and patient activated mode. This will cause the microprocessor to obtain those operating instructions from the external memory which correspond to the combined automatic and patient activated mode to be described hereinafter.

If the atrial defibrillator 330 is set into the automatic mode by the mode select stage 366, in accordance with step 414, the atrial defibrillator 330 will enter the automatic mode. In the automatic mode, the sequence initiating stage 360 causes the intervention sequencer 368 to perform the intervention sequence at spaced apart times and, preferably, predetermined times. To that end, a timer 362 is first reset and started in step 422. At this time, the activation control stage 364 maintains the sequence initiator 368 in the deactivated state.

When the sequence initiating stage 360 determines in step 424 that the timer 362 has timed out, the sequence initiating stage 360 then overrides the activation control stage 364 to activate the intervention sequencer 368. The atrial fibrillation detector 370 first, in step 426, determines if the atria are in need of cardioversion. If the atria are not in fibrillation, the process returns to step 422 to reset and start timer 362. However, if it is determined in step 426 that the atria are in need of cardioversion, the charge and delivery control stage 372, the charger and storage capacitor circuit 374, and the discharge circuit 376 cardiovert the atria in step 428 in a manner as previously described. After the cardioverting electrical energy is applied to the atria in step 428, the atrial fibrillation detector 370 once again determines if the atria are in fibrillation in accordance with step 430. If the atria are still in fibrillation, the sequence initiator 368 returns to step 428 to once again apply cardioverting electrical energy to the atria of the heart. However, if in step 430 the atrial fibrillation detector 370 fails to detect atrial fibrillation, the timer 362 is then reset and a new time period is begun.

From the above, it can be seen that the automatic mode will automatically, at predetermined times, determine if the atria are in fibrillation. If the atria are in fibrillation, cardioverting electrical energy is applied to the atria until the atrial fibrillation episode is terminated. Once the atrial fibrillation is terminated, the process returns to reset and start timer 362.

If the patient activated mode 416 is selected, the sequence initiating stage 460 in step 432 continuously detects for a sequence command generated from external to the patient. When the sequence command, such as a magnetic field generated by an external magnet of the type well known in the art is applied to the implantation site to close and then open read switch 363, the sequence command will have been detected and the sequence initiating stage causes the intervention sequence to be performed. To that end, in step 434, the atrial fibrillation detector 370 determines if the atria are in fibrillation and in need of cardioversion. If the atria are not in fibrillation, the process returns for the sequence initiating stage to once again detect a sequence command. However, if atria are in fibrillation, then in step 436, cardioverting electrical energy is applied to the heart. After the cardioverting electrical energy is applied to the heart, the atrial fibrillation detector 370 in step 438 determines if the atrial fibrillation episode has been terminated. If it has, the process returns for the sequence initiating stage to detect another sequence command. Of course, when the sequence initiating stage is detecting for a sequence command, the activation control stage 364 maintains the intervention sequencer 368 in the deactivated state. If the atrial fibrillation continues, after cardioversion, the atria are once again cardioverted in step 436. This process continues until the atrial fibrillation episode is terminated.

Although the intervention sequencer 368 is described above as continuously applying cardioverting electrical energy to the atria of the heart until the heart is successfully cardioverted, it is preferred that such applications of cardioverting electrical energy be limited to a specific number of such applications. To that end, as will be appreciated by those skilled in the art, the number of applications of the cardioverting energy may be counted, and when a predetermined count is reached, the process would then be returned to either reset and start the timer 362 when in the automatic mode, or return to detect another sequence command when in the patient activated mode.

If the atrial defibrillator is programmed into the combined automatic and patient activated mode, the timer 362 is first reset and started in step 440. While the timer 362 is timing a predetermined time period, the sequence initiating stage 360 continuously determines in step 442 if a sequence command has been received as previously described and, if not, if the timer 362 has timed out in accordance with step 444. The sequence initiating stage continues to perform steps 442 and 444 until either a sequence command is received or the timer 362 times out. If a sequence command is determined in step 442 to occur prior to the time-out of the timer 362, the sequence initiating stage 360 will first stop timer 362 in step 446 and then cause the intervention sequencer 368 to enter its intervention sequence by performing steps 434, 436 and 438, as previously described. When the intervention sequence is completed, the timer 362 is reset in step 440 and the process repeats.

If the timer 362 times out prior to the receipt of a sequence command, the sequence initiating stage will cause the intervention sequencer 368 to enter its intervention sequence by performing steps 426, 428 and 430, as previously described. Upon completion of the intervention sequence, the timer 62 is once again reset in step 440 and the process repeats.

Hence, from the above description, it will be noted that the combined automatic and patient activated mode causes the sequence initiating stage to initiate an intervention sequence upon either the receipt of a sequence command (patient activated mode) or upon the time out of the timer 362 (automatic mode). After the intervention sequence is completed, and regardless of whether the intervention sequence was initiated due to the receipt of a sequence command or the time out of the timer 362, the timer 362 is reset and started.

As can thus be seen, the present invention provides and atrial defibrillator having selectable modalities, including an automatic mode, a patient activated mode, and a combined automatic and patient activated mode. In the patient activated mode, while the patient is enabled to initiate an intervention sequence, this intervention sequence requires that the atrial defibrillator 330 first detect atrial fibrillation to confirm the patient's diagnoses before allowing cardioverting electrical energy to be applied to the patient's heart.

While particular embodiments of the present invention have been shown and described, modifications may be made. Hence, it is therefore intended in the appended claims to cover all such changes and modifications which fall within the true spirit and scope of the invention.

What is claimed is:

1. Apparatus for administering electrotherapy to a patient's heart to restore a normal heart rhythm comprising:

an unsophisticated primary detector means for detecting, with a first degree of precision, possible abnormalities in a patient's heart rhythm;

a sophisticated secondary detector means for analyzing the heart rhythm and more precisely identifying abnormalities therein, said secondary detector means being generally inactive in regard to detecting and analyzing abnormalities in the heart rhythm in the absence of a detection of a possible abnormality by said primary detector means;

means responsive to the detection of a possible abnormality in the heart rhythm by said primary detector means for activating said secondary detector means, said secondary detector means being constructed and arranged to analyze the patient's heart rhythm with a second degree of precision significantly higher than the first degree of precision exercised by said primary detector means in order to confirm said rhythm abnormality; and, means responsive to confirmation of said rhythm abnormality by said secondary detector means for delivering appropriate electrocardiac therapy to the heart.

* * * * *